US006217851B1

(12) United States Patent
Kleinberg et al.

(10) Patent No.: US 6,217,851 B1
(45) Date of Patent: *Apr. 17, 2001

(54) ANTI-CARIES ORAL COMPOSITIONS

(75) Inventors: Israel Kleinberg, Smithtown, NY (US); Ana Maria Acevedo, Caracas (VE); Robi Chatterjee, South Setanket, NY (US)

(73) Assignee: The Research Foundation of State University of New York, Stony Brook, NY (US)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 09/026,132

(22) Filed: Feb. 19, 1998

Related U.S. Application Data

(62) Division of application No. 08/611,206, filed on Mar. 5, 1996, now Pat. No. 5,762,911.

(51) Int. Cl.[7] .............................. A61K 7/16; A61K 33/10
(52) U.S. Cl. ............................................. 424/49; 424/687
(58) Field of Search ....................................... 424/49, 687

(56) References Cited

U.S. PATENT DOCUMENTS

| | | | |
|---|---|---|---|
| 3,932,608 | 1/1976 | Anderson et al. | 424/54 |
| 3,943,241 | 3/1976 | Anderson et al. | 424/54 |
| 4,064,138 | 12/1977 | Saari Albert et al. | 548/344 |
| 4,225,579 | * 9/1980 | Kleinberg | 424/48 |
| 4,367,218 | * 1/1983 | Jacobson | 424/49 |

FOREIGN PATENT DOCUMENTS

| | | |
|---|---|---|
| 0 569 666 | 11/1993 | (EP) . |
| 2 055 574 | 3/1981 | (GB) . |

OTHER PUBLICATIONS

Chemical Abstracts No. 72737a, vol. 106. No. 10, Mar. 9, 1987, by Tsujita Satoshi et al.

Supplementary European Search Report for European Application No. PCT/US97/05273 (5 pages) dated Oct. 9, 1999.

M.F. Cole and W.H. Bowen, "Effect of Sodium Phytate on the Chemical and Microbial Composition of Dental Plaque in the Monkey"—*J.Dent. Res.*, May–Jun. 1975, vol. 54, pp. 449–457.

*Chemistry and Applications of Phytic Acid: An Overview*—Edited by Ernst Graf, Pilatus Press, 1986—pp. 1–20.

H.W. Kaufman and I. Kleinberg, "X–ray Diffraction Study of the Effect of Phytate on the In Vitro Formation of Calcium Phosphates"—JADR *Abstracts*, 1973—p. 169.

H.W. Kaufman and I. Kleinberg, "Effect of pH on Calcium Binding By Phytic Acid and its Inositol Phosphoric Acid Derivatives and onthe Solubility of their Calcium Salts"—*Archs Oral Bio.*,—1971, vol. 16—pp. 445–460.

H.W. Kaufman and I. Kleinberg, "HYdrolysis of Phytate and its Inositol Phosphate Intermediates by an Acid and an Alkaline Phosphatase"—*Archs Oral Bio.*, 1975, vol. 20—pp. 157.

H.W. Kaufman and I. Kleinberg, "The Effect of pH on the Adsorption Properties of the Phytate Molecule", *Archs Oral Biol.*, vol. 15, 1970—pp. 917–934.

I. Kleinbergg, J.A. Kanapka, R. Chatterjee, D. Craw, N.D'Angelo and H.J. Sandham, "Metabolism of Nitrogen by the Oral Mixed Bacteria"—In: *Saliva and Dental Caries*—pp. 357–377 (1971).

D.S. Magrill, "The Reduction of the Solubility of Hydroxyapatite in Acid by Adsorption of Phytate from Solution", *Archs Oral Biol.*, vol. 18, 1973—pp. 591–600.

T.H. Grenby, "Tests of Sodium Phytate as a Protective Agent Against Dental Caries in the Rate", *Abstracts of Papers presented at the 18th ORCA Congress*, 1972—pp. 82–83.

Eugene R. Morris, "Phytate and Dietary Mineral Bioavailability", *Phytic Acid: Chemistry and Applications*—pp. 57–76. (1962).

Hakon Nordbo andGunnar Rolla, "Desprption of Salivary Proteins from Hydroxyapatite by Phytic Acid and Glycerophosphate andthe Plaque–Inhibiting Effect of the Two Compounds in Vivo", *J. Dent. Res*, May–Jun. 1972, vol. 3—pp. 800–802.

A. Wise, "Influence of Calcium on Trace Metal–Phytate Interactions", In: *Phytic Acid: Chemistry and Applications*, 1986, Edited by E. Graf, Pilatus Press, 1986—pp. 161–160.

\* cited by examiner

*Primary Examiner*—Kevin E. Weddington
(74) *Attorney, Agent, or Firm*—Darby & Darby

(57) ABSTRACT

The present invention relates to oral compositions containing anti-caries agents distributed in an oral vehicle. In particular, the present invention provides oral compositions containing calcium, arginine and a cariostatic anion distributed in an oral vehicle. A method for preparing oral compositions containing anti-caries agents is also provided by the present invention. A method of reducing dental caries is described which comprises delivering a therapeutically effective amount of an oral composition containing calcium, arginine and a cariostatic anion into the oral cavity.

30 Claims, 3 Drawing Sheets

FIG. I

ANTI-CARIES ORAL COMPOSITIONS

This is a division of application Ser. No. 08/611,206, filed Mar. 5, 1996 now U.S. Pat. No. 5,762,911. Each of these prior applications is hereby incorporated herein by reference, in its entirety.

FIELD OF THE INVENTION

Dental caries is a multi-factorial disease which occurs when cariogenic oral bacteria metabolize simple and complex sugars to produce acids which cause the dissolution of tooth enamel, thereby creating a caries lesion or cavity. The present invention provides oral compositions containing anti-caries agents distributed in an oral vehicle. In particular, the present invention describes oral compositions containing calcium, arginine, and a cariostatic anion distributed in an oral vehicle. A method for preparing oral compositions containing anti-caries agents is also described by the present invention. A method of reducing dental caries is described which comprises delivering a therapeutically effective amount of an oral composition containing calcium, arginine and a cariostatic anion into the oral cavity.

BACKGROUND OF THE INVENTION

Ever since Miller in 1890 first provided evidence that acid produced by the oral bacteria during the fermentation of carbohydrates is mainly responsible for the demineralization of teeth and the initiation of the dental caries process, the ability to retard or prevent the demineralization of teeth has been extensively studied. Miller W. D. (1890) "Microorganisms of the human mouth," Reprinted 1973. Karger, Basel. Miller described the formation of dental caries as a two step process. In the first step, oral bacteria, primarily Gram-positive bacteria, metabolize fermentable carbohydrates present in the oral cavity to produce acid. In the second step, the acids generated by the oral bacteria demineralize tooth enamel, dentine and/or cementum, thereby creating a caries lesion or cavity in the tooth crown or root.

The primary source of fermentable carbohydrates metabolized by the oral bacteria in the first step of the Miller process is the diet. Glucose is the main sugar available from dietary carbohydrates. It is a constituent monosaccharide of sucrose, maltose, lactose and starch. Studies on pure cultures of oral bacteria have shown that glucose is readily fermented by the Gram-positive bacteria which contribute far more to the fermentation process than oral Gram-negatives. Such fermentation can be arbitrarily classified as either homofermentative, where lactic acid is the main product, or heterofermentative, where substantial amounts of products other than lactic, including formic, acetic, propionic and succinic acids, as well as ethanol and carbon dioxide can be produced. Platt and Foster (1958) *J. Bacteriol.*, 75:453–459.

Investigators have tried with varying degrees of success to reduce acid production by the microorganisms present in dental plaque. Jenkins G. N. (1978) *The Physiology and Biochemistry of the Mouth*, 4th Ed., Oxford, England, Blackwell, pp. 414–500. These have included methods that try to (i) reduce the availability of fermentable carbohydrate from the diet, (ii) reduce the amount of plaque and the number of acidogenic bacteria in dental plaque, (iii) interfere with specific bacteria, (iv) interfere with bacterial glycolysis, the metabolic process by which the plaque bacteria make acid from carbohydrates, (v) neutralize the acids formed during glycolysis, and (vi) stimulate formation of base by the plaque bacteria mainly from urea and arginine to counter the acid formation characteristic of the caries process. Kleinberg et al. (1979) "Metabolism of nitrogen by the oral mixed bacteria". In: *Saliva and Dental Caries* (Edited by Kleinberg et al.) pp.357–377, Information Retrieval, Washington D.C. These methods however, have had limited success in reducing dental caries.

Researchers have had greater success in reducing or preventing dental caries by combating the second step of the Miller dental caries formation process, namely, reducing the dissolution of enamel mineral by reducing the solubility of enamel using fluoride. Numerous studies have examined therapeutics which inhibit the dissolution of dental enamel by the acid generated by plaque bacteria. Fluoride has proven to be the most effective therapeutic. Newburn (1986) *Fluorides and Dental Caries*, 3rd. Ed., Springfield, Ill., Charles Thomas. Fluoride has been found to inhibit the dissolution of enamel by dental plaque acids by reducing the rate of solubilization, increasing remineralization and altering the solubility product of the calcium phosphate that constitutes most of the mineral in enamel, cementum and dentine. To a much lesser degree, fluoride also affects bacterial transport of sugars and the glycolytic process. Hamilton (1969) *Can. J. Microbiol.*, 15:1021–1027.

Although various therapeutic agents have been examined for their ability to prevent dental caries, the incidence of dental caries remains unacceptably high, particularly in third world countries and in individuals with saliva deficiencies, especially adults on saliva inhibiting medications. One reason for the failure of conventional therapeutics to adequately retard dental caries is that these dental therapeutics primarily focus on the second step of the Miller dental caries process and have failed to provide therapeutics that adequately address the fact that dental caries is a multi-factorial disease and needs a multi-factorial approach. Hence, it is not surprising that reduction of the solubility of tooth enamel using fluoride has resulted in a limited reduction in dental caries in a range of approximately 20% to 40%. Few attempts have been made to develop agents that can simultaneously affect both the acid production and the enamel demineralization processes.

The present invention alleviates many of the problems associated with current therapies for preventing dental caries. In particular, the oral compositions provided by the present invention combat the dental caries process at both stages described by Miller. Specifically, the cariostatic oral compositions described herein contain therapeutic amounts of calcium, arginine and a cariostatic anion. These compounds may interact to form an anti-caries complex.

Arginine favors the formation of base by the dental plaque bacteria and the proliferation of an alkali producing microflora in plaque. Kanapka and Kleinberg (1983) *Archs. oral Biol.* 28, 1007–1015. The acids produced by many of the plaque bacteria are neutralized by the alkli compounds produced from arginine, whether or not the amino acid is found free or becomes available from peptides or proteins, especially from saliva. Kleinberg et al. (1979) "Metabolism of nitrogen by the oral mixed bacteria" In: *Saliva and Dental Caries* (Edited by Kleinberg et al.) pp. 357–377, Information Retrieval, Washington, D.C. Thus, the arginine component of the composition described herein attacks the first stage of the Miller process.

Calcium is another component of the oral compositions of the invention. Calcium suppresses the solubilization of tooth enamel by mass action and reduces the release of calcium from tooth enamel when attacked by acid. Calcium precedes the release of phosphate from enamel, dentine and other calcium phosphate containing tissues during acid solubilization. Thus, the calcium component of the composition described herein attacks the second stage of the Miller caries process.

The cariostatic anions of the oral compositions of the present invention may attack both stages of the caries process. Cariostatic anions may (i) provide buffering which enhance the acid neutralizing activity of the arginine as well as neutralizing the acid itself, (ii) provide an organic phosphate source to act as a surface covering or "poison" or to be hydrolyzed by the plaque bacteria to release inorganic orthophosphate which inhibits tooth dissolution and enhances tooth remineralization or (iii) do both. Unlike conventional oral compositions, the oral compositions described by the present invention contain components that are coordinated to significantly reduce dental caries by attacking the formation of caries lesions at both steps of the Miller caries formation process.

SUMMARY OF THE INVENTION

The present invention relates to oral compositions containing therapeutic amounts of calcium, arginine and a cariostatic anion distributed in an oral vehicle. In one preferred embodiment, the oral composition is supplemented with fluoride.

The present invention further relates to a method of preparing oral compositions containing anti-caries agents.

Yet another aspect of this invention is directed to a method of reducing dental caries comprising delivering a therapeutically effective amount of an oral composition containing calcium, arginine and a cariostatic anion into the oral cavity. In one preferred embodiment, the oral compositions used in the method described herein further contains fluoride.

DETAILED DESCRIPTION OF THE INVENTION

Figure 1:
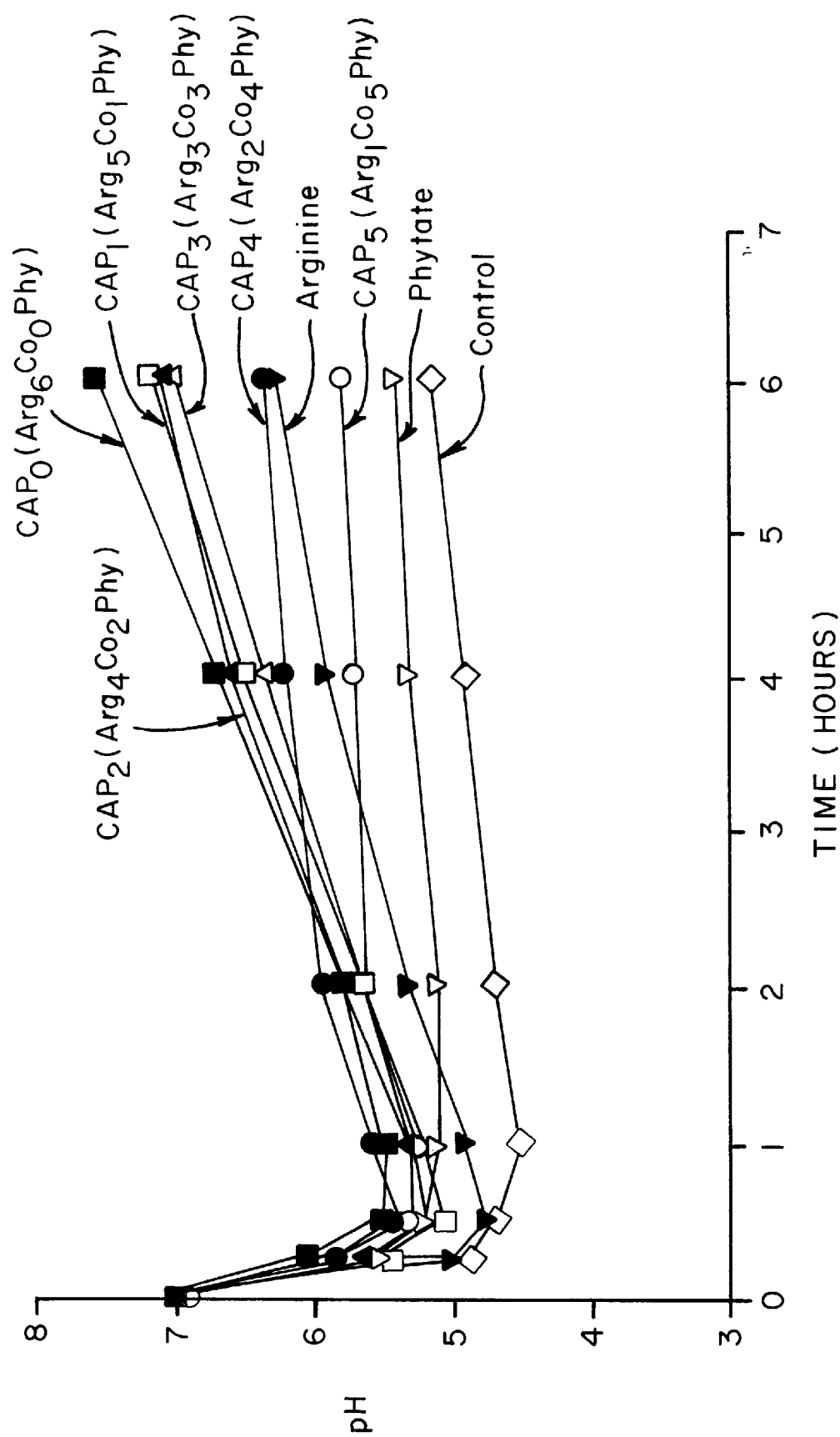
FIG. 1 shows the pH response of salivary sediment incubated with 5.6 mM glucose in the presence of a series of calcium arginine phytate (CAP) complexes. The cariostatic anion is phytate and the calcium and arginine vary reciprocally. Arginine phytate is considered a CAP complex with the calcium concentration zero. Controls include incubation mixtures with phytate alone and arginine alone. At this sugar concentration, one type of in vivo plaque pH response is observed.

The present invention is directed to oral compositions containing anti-caries agents distributed in an oral vehicle. In particular, the present invention describes oral compositions containing therapeutic amounts of calcium, arginine and cariostatic anion distributed in an oral vehicle. The term "cariostatic" denotes agents which are capable of retarding or preventing dental caries including remineralization of caries lesions. As defined herein, a cariostatic anion is a biologically compatible anion capable of enhancing the anti-caries activities of calcium and arginine. Evidence of anions which are capable of enhancing the anti-caries activities include, for example, anions which, when added to a composition containing calcium and arginine, retard or prevent dental caries better than the same oral composition without the cariostatic anion. Biologically compatible anions are anions that may be administered to a mammal orally without an adverse reaction. Examples of cariostatic anions include, for example, bicarbonate, carbonate, glycerophosphate, phytate and its inositol phosphate derivatives, and the like.

Acceptable oral vehicles include, for example, any conventional oral delivery system, such as dental care products, food products and chewing gum. Examples of dental care products include, for example, dentifrices, solutions or pastes, mouthwashes in the form of liquids, powders, gels or tablets, and dental flosses. Examples of food products which contain the oral compositions described herein include, for example, lozenges and confectioneries.

A therapeutic amount of calcium, arginine and a cariostatic anion as defined by this invention is an amount of these anti-caries agents sufficient to neutralize the acids produced by the dental plaque as a result of their metabolism of carbohydrate and simultaneously reduce demineralization or increase remineralization of the dental enamel. For example, a dentifrice may contain anti-caries agents in an amount ranging from 0.5 to 4% (V/V) and preferably from 1 to 3% (V/V); a mouthwash may contain anti-caries agents in an amount ranging from 0.5 to 3.5% (V/V) and preferably from 1 to 3%.

In one preferred embodiment, the oral compositions contain calcium in an amount ranging from 5 $\mu$g/mg to 200 $\mu$g/mg, arginine in an amount ranging from 5 $\mu$g/mg to 700 $\mu$g/mg and phytate in an amount ranging from 5 $\mu$g/mg to 600 $\mu$g/mg or bicarbonate in an amount ranging from 5 $\mu$g/mg to 200 $\mu$g/mg or carbonate in an amount ranging from 5 $\mu$g/mg to 200 $\mu$/mg. In a more preferred embodiment, the oral compositions further contain fluoride in an amount ranging from 200 to 1500 ppm.

The present invention is further directed to a method of preparing oral compositions containing anti-caries agents. In particular, a method of preparing oral compositions containing therapeutic amounts of calcium, arginine and a cariostatic anion distributed in an oral vehicle is described by the present invention. The method used to produce the oral compositions depends upon the oral vehicle used and solubility requirements for the anti-caries agents. In one embodiment, the acid form of the cariostatic anion may be initially titrated with an arginine free base such as arginine hydroxide followed by titration with calcium hydroxide. In another embodiment, the acid form of the cariostatic anion may be titrated to the desired pH of the oral composition with arginine hydroxide and one or more calcium containing compounds such as calcium carbonate. The anti-caries agents may also be prepared by titrating the cariostatic anion to the desired pH of the oral composition. The composition formed is dried and calcium in the form of a powder is added and thoroughly mixed with the composition. When the cariostatic anion forms a soluble salt with calcium, arginine additions may follow calcium additions. When the cariostatic anion is bicarbonate or carbonate, the oral composition may be prepared necessarily by first titrating the bicarbonate or carbonate with arginine rather than calcium due to the poor solubility of calcium carbonate and the high solubility of arginine bicarbonate.

Arginine bicarbonate may be prepared initially from arginine hydroxide by bubbling carbon dioxide or by adding dry ice in excess into a solution of arginine free base. The calcium component of the oral composition may be added as calcium. Preferred examples of calcium containing compounds which may be used to form the oral composition of the present invention include, for example, a soluble calcium organic phosphate, a poorly soluble calcium organic phosphate or calcium carbonate. The calcium carbonate is a preferred embodiment when the oral vehicle is a dentifrice. Calcium carbonate is a known polishing agent.

The anti-caries agents in the oral composition of the present invention may interact to form a complex compound. For example, when the cariostatic anion is phytate, calcium and arginine may bind to phytate to form a calcium arginine phytate complex (CAP complex).

In addition to the anti-caries agents, the oral compositions described in accordance with the present invention may contain any conventional ingredient for the particular oral vehicle. For example, liquid mouthwashes may contain a solvent such as distilled or deionized water, ethanol and the like; a sweetening agent such as saccharine, aspartame and the like; and a flavoring agent such as peppermint oil, spearmint oil and the like. Dentifrice pastes or gels may contain, for example, water, glycerine or sorbitol, a conventional abrasive such as calcium pyrophosphate, aluminum hydroxide, resins, insoluble alkali metal metaphosphates and the like in a standard amount of 20–60% wt.; a binder such as hydroxyethyl cellulose, xanthin gum, sodium carboxymethyl cellulose and the like in a standard amount of 0.5–5.0% wt.; a foaming agent such as sodium lauryl sulfate, sodium coconut monoglyceride sulfonate, sodium-N-methyl-N-palmitoyl tauride and the like in a standard amount of 0.5–3.0% wt.; a flavoring agent; a sweetening agent; an antiseptic agent and any other ingredient required for the particular formulation. Dentifrice powders may contain in addition to the anti-caries agents, a conventional abrasive and a flavoring agent. Tablets and powders may contain, for example, a vehicle such as lactose, mannitol and the like; a binder such as corn starch, carboxymethyl cellulose and the like; and a disintegrator.

The oral compositions described by the present invention may be applied orally without decalcifying or otherwise damaging dental enamel. The pH of the oral compositions of the present invention generally ranges from about 6.0 to about 9.0. In one embodiment, the pH of the oral composition ranges from about 7.0 to about 8.0. The pH of the oral compositions described herein can be controlled with acid such as hydrochloric or with base such as sodium hydroxide.

The invention is further directed to a method of reducing dental caries comprising delivering a therapeutically effective amount of the oral compositions of this invention into the oral cavity. A therapeutically effective amount of oral composition as defined by the present invention is a quantity of oral composition capable of retarding or preventing dental caries by reducing or neutralizing the acids produced by the dental plaque as a result of carbohydrate metabolism and simultaneously reducing demineralization of the dental enamel, dentine and cementum by providing calcium to suppress solubilization of the tooth by mass action or by favoring remineralization. For example, a dentifrice delivered according to the method of the present invention may contain anti-caries agents in an amount ranging from 0.5 to 4% and preferably from 1 to 3%. A mouthwash may contain anti-caries agents in an amount ranging from 0.5 to 3.5% and preferably from 1.0 to 3.0%.

Without being bound to a theory, it is believed that when the cariostatic anion is an organic phosphate, the cariostatic anion may reduce tooth demineralization by providing a surface poison on the tooth enamel and by hydrolyzing to orthophosphate which suppresses the solubilization of tooth enamel by mass action. When the cariostatic anion bicarbonate or carbonate, it is believed that the bicarbonate or carbonate anion may reduce demineralization by three means. The first is by providing buffering that reduces the amount of acid in dental plaque and on the tooth surface available for dissolution of tooth mineral. The second is by enhancing the acid neutralizing activity of arginine by maintaining the pH near the optimum pH for the degradation of arginine by the plaque bacteria (between about 7.0 and 8.0). The third is by reducing the concentration of carbon dioxide when acid is neutralized and producing calcium hydroxide to remineralize the dental enamel.

The present invention further provides an article of manufacture comprising a packaging material and the oral compositions described herein contained within said packaging material, wherein said oral composition is effective in retarding or preventing dental caries and wherein said packaging material contains a label that indicates that said oral composition is effective in retarding or preventing dental caries. The packaging material used to contain the oral compositions can comprise glass, plastic, metal or any other suitably inert material. For example, a dentifrice containing the oral composition of the present invention may be contained in a collapsible tube, typically aluminum, lined lead or plastic or a squeeze pump or pressurized dispenser to measure out the contents or in a tearable sachet.

In order to further illustrate the present invention, the experiments described in the following examples were carried out. It should be understood that the invention is not limited to the specific examples or the details described therein. The results obtained from the experiments described in the examples are shown in the accompanying figures and tables.

EXAMPLE I

This example shows a method of preparing anti-caries agents containing arginine phytate and calcium arginine phytate suitable for this invention. These anti-caries agents are also referred to as calcium arginine phytate (CAP) salts. In the first step, phytic acid was prepared from sodium phytate using the procedure of Harrison and Mellanby (1939) *Biochem J.*, 33:1660–1680 as modified by Kaufman and Kleinberg (1971) *Archs Oral Biol.* 16: 445–460. The methodology of these references is incorporated by reference.

Approximately 100 g of sodium or calcium phytate (purchased from Nutritional Biochemicals, Cleveland, Ohio) was dissolved in 200 ml distilled water and the pH was adjusted to 1.0 with concentrated HCl. Ferric chloride (0.26 M) was then added, causing the formation of a white precipitate of ferric phytate. The precipitate was then separated from the liquid phase by centrifugation. The supernatant was subsequently discarded. The precipitate was then washed three times using approximately 1.5 liter of distilled water for each washing. The precipitate was suspended in distilled water and the pH of the solution was adjusted to between 11.0 and 12.0 with NaOH. A flocculent precipitate of ferric hydroxide formed. The precipitate was sedimented by centrifugation at 1600 g for 20 min. The supernatant was decanted and the precipitate washed once with 0.1 N NaOH. The washing and supernatant were combined and the precipitation process repeated twice.

The sodium phytate solution was then put through a Dowex cation exchange resin (BioRad 50W-x8, 100–200 mesh, $H^+$ form; purchased from Calbiochem, Los Angeles, Calif.), converting the phytate to phytic acid. Analysis for inorganic and total phosphorus showed a phytic acid concentration of 0.011 M and an inorganic orthophosphate ($P_1$) concentration of 0.002 M which is approximately 3 percent of the total phosphorus concentration.

The percentage of the total phosphorus present as $P_1$ was reduced from 3 percent to 0.1 percent of the total using the following procedure. An aliquot, usually 20 ml of the stock 0.011 M solution of phytic acid was run through a glass column (1.0×30 cm) containing a Dowex anion exchange resin (BioRad AG 1-x8, 200–400 mesh, $Cl^-$ form; purchased from Calbiochem, Los Angeles). Initial elution with 50 ml of 0.25 M LiCl, eluted $P_1$; subsequent elution with 40 ml of 1.0 M LiCl, eluted the phytate.

The phytate fraction was lyophilized and the LiCl in the fraction removed by washing the residue 6 times with 5 ml volumes of absolute methanol. Residual methanol was removed by evaporation with a stream of air. The phytate that remained was present as the lithium phytate salt, which was then dissolved in 10 ml of distilled water.

The lithium phytate was converted to phytic acid by running the lithium phytate solution through a glass column (1.0×30 cm) containing a Dowex cation exchange resin (50-x8, $H^+$ form) and eluting with 20 ml of distilled water. The eluate was lyophilized to concentrate the phytic acid and to remove residual HCl. The residue was dissolved and lyophilized 6 times to ensure complete removal of HCl.

Analysis of the resulting aqueous solution of phytic acid for organic and inorganic phosphorus showed a phytic acid molar concentration of 59.3 mM. The inorganic phosphorus molar concentration was 3.8 mM. At this concentration, only 1.05% of the total phosphorus is present as inorganic phosphorus.

Following the preparation of phytic acid, 10 ml of phytic acid was titrated with arginine hydroxide (0.5M) to pH 7.0. The titration was repeated by gradually adding arginine hydroxide to separate aliquots of phytic acid in equal molar stepped amounts. This was done because preliminary experiments indicated that arginine surprisingly behaves in the titration as though it has a valence of one.

To prepare calcium arginine phytate salts, arginine phytate was initially prepared with stepped amounts of arginine as described above. The arginine phytate was then titrated to pH 7.0 with freshly prepared saturated $Ca(OH)_2$ at a concentration of 0.02 M. The pH of the titrate was measured in each titration with a combined glass and calomel pH electrode.

Following the preparation of arginine phytate and calcium arginine phytate, the compounds were lyophilized for 36 hours to dryness (Virtis lyophilizer, Virtis, Gardiner, N.Y.). All compounds were analyzed for inorganic and organic phosphorus and total nitrogen. The calcium arginine phytate compounds were further analyzed for calcium.

The amount of arginine present in each compound was determined by measuring the nitrogen concentration using the Nessler's method after sulfuric acid-peroxide digestion as described by Singer and Kleinberg (1983) *Archs. oral Biol.* 28: 873–878. This reference is incorporated herein by reference.

The amount of calcium present in the calcium arginine phytate compounds was determined by analyzing the compounds using the Perkin-Elmer 330 atomic absorption spectrophotometer and the Perkin-Elmer Manual of Analytical Methods for Atomic Absorption Spectrophotometry.

The amounts of inorganic and organic phosphorus were determined by the method described by Chen et al. (1956) *Anal. Chem.*, 28:1756–1758 which is incorporated herein by reference. Briefly, the amount of inorganic phosphorus in each compound was determined by measuring with a spectrophotometer the color that develops at 600 nm when an aqueous ammonium molybdate solution followed by sulfuric acid is added to an aqueous solution of the compound. The amount of organic phosphorus is determined in the same manner after the compound has been hydrolyzed by perchloric and sulfuric acids.

For the analysis of calcium, phosphorus and nitrogen, 0.2 mg of each compound was dissolved in distilled water. When the solubilization was complete, the suspensions were centrifuged at 9,000 g for 5 minutes in the Beckman 152 Microfuge prior to analysis. The centrifugates were then dissolved in acetic acid buffer at pH 4.0 and similarly analyzed. Although all of the compositions readily dissolve in acid, the two stage analysis was done to determine the solubility/insolubility components of neutral preparations of each composition.

Because phytate is multivalent, it is able to carry both arginine and calcium as cations in various proportions. The more calcium that binds to the complex, the less soluble the complex becomes while the more arginine that binds to the complex, the more soluble the complex becomes. (see Tables 1–4).

TABLE 1

The pH at and above which precipitation of CAP salts of different calcium/arginine/phytate molar ratios occurs.

| Compounds | Precipitating pH |
|---|---|
| $CAP_0$ | *** |
| $CAP_1$ | *** |
| $CAP_2$ | 6.80 |
| $CAP_3$ | 6.09 |
| $CAP_4$ | 5.62 |
| $CAP_5$ | 5.00 |

*** no precipitation at least up to pH 7.0. The lower the precipitating pH in this type of titration experiment, the lower the salt solubility.

TABLE 2

Calcium content of arginine phytate and each of the 5 different CAP salts that were prepared. Results are means of 3 analyses ± SEM.

| | Calcium (μg/mg of CAP composition dry weight) | | |
|---|---|---|---|
| Compound | Supernatant | Precipitate | Total Sup + ppte |
| $CAP_0$ | 0.0 | *** | 0.0 |
| $CAP_1$ | 11.1 ± 0.3 | *** | 11.1 |
| $CAP_2$ | 13.2 ± 1.3 | 11.6 ± 1.9 | 24.8 |
| $CAP_3$ | 17.4 ± 1.3 | 29.5 ± 2.2 | 47.0 |
| $CAP_4$ | 14.9 ± 1.3 | 38.6 ± 2.2 | 53.5 |
| $CAP_5$ | 10.3 ± 0.7 | 144.7 ± 0.0 | 155.0 |

*** no precipitate

TABLE 3

Arginine content of arginine phytate and each of the 5 different CAP salts that were prepared. Results are means of 3 analyses ± SEM.

| | Arginine ($\mu$g/mg of CAP composition dry weight) | | |
|---|---|---|---|
| Compound | Supernatant | Precipitate | Total Sup ± ppte |
| $CAP_0$ | 681.8 | *** | 681.8 |
| $CAP_1$ | 681.8 ± 12.4 | *** | 681.8 |
| $CAP_2$ | 524.8 ± 3.4 | 0.0 | 524.8 |
| $CAP_3$ | 472.4 ± 4.9 | 5.2 ± 1.7 | 477.7 |
| $CAP_4$ | 372.8 ± 4.6 | 8.8 ± 1.3 | 381.5 |
| $CAP_5$ | 192.3 ± 4.8 | 41.4 ± 0.5 | 233.7 |

*** no precipitate

TABLE 4

Phytate content of arginine phytate and each of the 5 different CAP salts that were prepared. Results are means of analyses ± SEM.

| | Phytate ($\mu$g/mg of CAP composition dry weight) | | |
|---|---|---|---|
| Compound | Supernatant | Precipitate | Total Sup ± ppte |
| $CAP_0$ | 307.6 | *** | 307.6 |
| $CAP_1$ | 307.6 | *** | 307.6 |
| $CAP_2$ | 292.9 | 0.0 | 292.9 |
| $CAP_3$ | 290.7 | 59.6 | 350.3 |
| $CAP_4$ | 231.9 | 96.8 | 328.7 |
| $CAP_5$ | 180.1 | 315.2 | 495.3 |

*** no precipitate

EXAMPLE II

This example shows a method of preparing calcium arginine bicarbonate/carbonate oral compositions suitable for this invention. In the first step, arginine bicarbonate is prepared by dissolving 15 grams of arginine free base (arginine hydroxide) in 100 ml of distilled water, which has a pH of 10.5 and then adding carbon dioxide in either gaseous form or solid form (dry ice) until the pH decreases to 8.5. At this pH, all of the arginine hydroxide is converted to arginine bicarbonate. When dry ice is added, it is inserted in successive pieces into the arginine hydroxide solution until the arginine hydroxide is converted to arginine bicarbonate. The arginine bicarbonate solution is then dried using conventional techniques. Finally, calcium carbonate powder is mixed with the arginine bicarbonate powder to produce a calcium arginine bicarbonate/carbonate composition in the proportions needed for a particular formulation, for example, one part calcium carbonate powder with one part arginine bicarbonate powder.

EXAMPLE III

This example demonstrates the ability of calcium arginine phytate of the present invention to retard the demineralization of enamel in vitro. Specifically, this example shows the ability of calcium arginine phytate to retard the demineralization of extracted molar teeth incubated with oral bacteria and a sugar source.

The molar teeth were incubated in a model simulating mixed microbial metabolism in the oral cavity developed by Kleinberg et al. (1973) *Archs. oral Biol.*, 18:787–798. This model utilizes the mixed oral bacteria in salivary sediment. The salivary sediment model used is recognized in the art as an effective proxy for the kinds of pH changes seen in the oral cavity and important in dental caries formation.

To collect salivary sediment, saliva stimulated by chewing paraffin wax was expectorated into test tubes chilled in cracked ice. The donors had not eaten for at least 12 h and had not brushed their teeth for 24 h prior to collection. The donors were instructed to fast for at least 12 h to provide stimulated whole saliva which contains a minimal level of exogenous carbohydrate. Kleinberg and Jenkins (1964) *Archs. oral Biol.*, 9:493–516. Following collection, the saliva was centrifuged at 1740 g for 15 min and the supernatant was subsequently removed by suction. Next, the sediment was washed three times with ice cold distilled water to remove any residual salivary supernatant. The washed salivary sediment was chilled in crushed ice until the assay was run.

The assay also required preparing sections of human molar teeth. Permanent molar teeth previously stored in distilled water free from microscopic cracks and decay on the occlusal, buccal or lingual surfaces were carefully cleaned with pumice using a rotating rubber cup. Following the cleaning, each tooth was sectioned vertically in a mesiodistal direction using a slow-speed saw with a circular diamond blade (Buehler Isomet, Buehler LTD., Evanstan, Ill.) which was cooled with 1% aerosol TO solution (Fisher Scientific, Springfield, N.J.). Slices of between 300–500 $\mu$m were obtained. The roots were cut off, the dentin and any area which was demineralized was covered with varnish, leaving only sound enamel exposed.

Following the preparation of the salivary sediment and the enamel sections, the demineralization assay was run. Prior to incubating the samples and running the assay, the washed salivary sediment was re-suspended in distilled water to a final concentration of 50 percent (v/v). For initial experiments that examined pH responses, incubation mixtures (600 $\mu$l) were prepared in 10×75 mm test tubes containing sediment at 16.7% (v/v), glucose at either 5.6 or 28.0 mM, and arginine phytate or calcium arginine phytate at a final concentration of 3.0 mM. Controls included incubation mixtures containing (1) sediment and glucose, (2) sediment, glucose and sodium phytate (3.0 mM) and (3) in some experiments, sediment, glucose and arginine. The range of glucose concentrations selected produced the two types of pH curves seen in vitro when plaque is challenged with fermentable carbohydrate. Kleinberg et al. (1973) *Archs. oral Biol.*, 18:787–798 and Kleinberg et al. (1977) *Caries Res.*, 11(Suppl.):292–320. The mixtures were incubated for 6 hours at 37° C. in a water bath. With 5.6 mM as with other low glucose levels, the pH rapidly fell, reached a minimum and then showed a slow progressive return towards baseline (see FIG. 1). With 28 mM glucose levels as with other high glucose levels, the pH also fell rapidly but it fell lower and showed little or no subsequent rise during the remainder of the experimental period (see FIG. 2) because glucose is still present to continue the acid formation and maintenance of the acidic pH. All incubation mixture preparations were done with the test tubes chilled in cracked ice until they were transferred to a 37° C. water bath for the incubation.

In each experiment, control samples without tooth slices were run. The mixtures with the slices were used to assess the effects of arginine phytate and the calcium arginine phytate (CAP) compounds on enamel demineralization. The mixtures without the slices were used to assess the calcium and phosphate released from non-dental enamel sources. Such sources may include calcium or phosphate ions in the sediment, small amounts of residual phosphate from arginine phytate or CAP complexes, and calcium from the CAP complexes.

Prior to the incubation, the pH of each mixture was adjusted to 7.0 using either 1.0 M HCl or NaOH. The dental enamel slices were added to one half of the mixtures. After the enamel slices were added, all the mixtures were immediately incubated in a water bath at 37° C. for 6 hours with occasional shaking. The pH was recorded at the onset of the incubation and at 1, 2, 4 and 6 hours thereafter using combined glass and calomel electrodes connected to a Radiometer pH meter. At the same time intervals, samples (60 μl) were withdrawn from each mixture and centrifuged in a micro-centrifuge (152 Microfuge, Beckman) at 7700 g for 3 min. The supernatant of each sample was carefully removed by suction and stored at 4° C. for subsequent analysis for calcium and inorganic phosphorus as described above. In incubation mixtures with dental enamel, the enamel was examined for demineralization (increased chalkiness) under a binocular microscope at the end of the incubation. Demineralization was scored on a scale of 0 to 4, where 0 indicated no demineralization and 4 indicated significant demineralization.

The calcium, phosphorus and phytate contents of arginine phytate (designated as $CAP_0$) and the five CAP complexes (designated as $CAP_1$–$CAP_5$) prepared for the incubation experiment are shown in Tables 2–4. The $CAP_0$ to $CAP_5$ complexes contained increasing amounts of calcium and decreasing amounts of arginine. The phytate content was approximately similar for all the complexes except the complex, $CAP_3$. The calcium varied from 0 to 155.0 μg per mg of complex. The arginine concentration varied from 233.7 to 691.8 μg per mg of complex.

Figure 2:
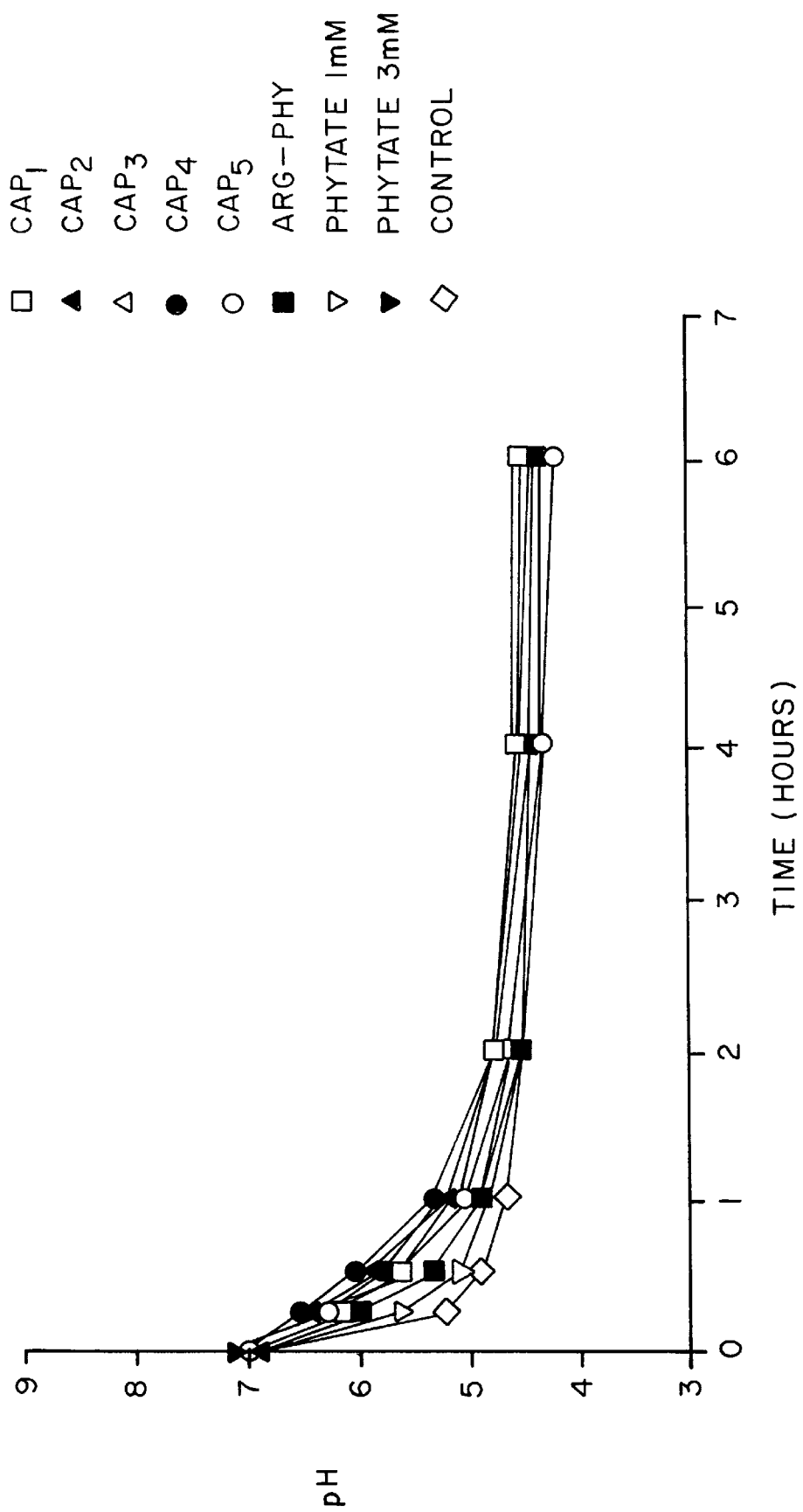
FIG. 2 shows the pH response of salivary sediment incubated with 28.0 mM glucose in the presence of a series of CAP complexes. The cariostatic anion is phytate and the calcium and arginine vary reciprocally. Arginine phytate is considered a CAP complex with the calcium concentration zero. Controls include incubation mixtures with phytate alone and arginine alone. At this sugar concentration, the second type of in vivo plaque pH response is observed.

The effects of arginine phytate ($CAP_0$) and the calcium arginine phytates ($CAP_1$ to $CAP_5$) on the pH of incubation mixtures incubated with low and high (5.6 and 28.0 mM) glucose are shown in FIGS. 1 and 2. With 5.6 mM glucose (FIG. 1), the pH rapidly fell and reached a minimum after 30 minutes to one hour of incubation. The most significant falls in the pH occurred in mixtures containing only sediment and glucose (control). The most significant rise in pH occurred in CAP mixtures containing the most arginine. The greater rise in pH with these arginine phytate compositions results from the phytate buffering enabling the arginine to function at a more favorable pH in the oral cavity for base formation. The incubation mixture containing $CAP_5$, which contained the least amount of arginine of the five CAP compositions, showed almost no pH-rise (FIG. 1). These results demonstrate the ability of arginine phytate and calcium arginine phytate complexes described by the present invention to counter the acid generated during the catabolism of glucose by the oral bacteria.

The demineralization of enamel during the incubation of salivary sediment and glucose for the various incubations is shown in Tables 5 and 6. Tables 5 and 6 show the calcium and phosphate released from tooth enamel incubated in salivary sediment-glucose mixtures (5.6 mM) in the absence and presence of arginine, phytate, arginine phytate and the various CAP complexes.

The mixtures containing 5.6 mM glucose, arginine phytate and the various CAP complexes showed a reduction in the amount of calcium and phosphate released from enamel at the end of the 6 h incubation compared to the no addition and phytate and arginine controls (Tables 5 and 6). Compared to the sediment-glucose control, reduction in solubilization with the various CAP compounds ranged from 91.2 to 100% for calcium (Table 5) and from 60.1 to 97.0% for phosphorous (Table 6). Arginine phytate ($CAP_0$) was less. Arginine alone showed some inhibition of enamel demineralization but the effects were less than with the arginine phytate and CAP complexes. Phytate alone was not effective.

TABLE 5

Calcium from enamel incubated in 5.6 mM glucose mixtures in the presence of various CAP salts.

| | Calcium (μg/ml) | |
|---|---|---|
| Compound tested | Mean ± SEM | % inhibition |
| $CAP_0$ | 23.2 | 85.8 |
| $CAP_1$ | 6.3 | 96.1 |
| $CAP_2$ | 2.4 | 98.5 |
| $CAP_3$ | 0.0 | 100.0 |
| $CAP_4$ | 14.3 | 91.2 |
| $CAP_5$ | 13.4 | 91.8 |
| Arginine | 67.1 | 58.8 |
| Phytate | 112.6 | 30.9 |
| Control | 163.0 | 0.0 |

TABLE 6

Phosphorus from enamel incubated in 5.6 mM glucose mixtures in the presence of various CAP salts.

| | Phosphorus (μg/ml) | |
|---|---|---|
| Compound tested | Mean ± SEM | % inhibition |
| $CAP_0$ | 25.2 | 35.8 |
| $CAP_1$ | 15.6 | 60.1 |
| $CAP_2$ | 10.1 | 74.3 |
| $CAP_3$ | 9.7 | 75.2 |
| $CAP_4$ | 1.3 | 97.0 |
| $CAP_5$ | 3.6 | 91.0 |
| Arginine | 24.1 | 38.5 |
| Phytate | 39.7 | 0.0 |
| Control | 39.2 | 0.0 |

Direct examination of the tooth slices showed differences between controls and CAP salts.

These results clearly demonstrate the ability of arginine phytate and calcium arginine phytate complexes to retard the demineralization of dental enamel during carbohydrate metabolism.

The effects of severe and prolonged acid pH on the ability of arginine phytate and CAP complexes to retard the demineralization of tooth enamel is shown in Tables 7 and 8. Such conditions occur in the mouth in poorly accessible dentition sites when fermentable carbohydrate is available to the plaque bacteria at high concentration and for prolonged periods of time (see FIG. 2). Acetate buffer was used to maintain the pH at 5.0 during the duration of the respective incubation mixtures. As shown in these tables, arginine phytate and the CAP compositions were inhibitory of the significant solubilization of calcium and phosphate that occurs at acidic pH. Sodium phytate was almost as effective as these compounds at low pH, supporting its role in reducing solubilization. Arginine alone was ineffective since there are no bacteria present to produce alkaline end-products therefrom.

Visual examination under a binocular dissecting microscope of the tooth slices, run at pH 4.0, 5.0 and 6.0 generally supported these effects (Table 9).

These studies clearly demonstrate the ability of arginine phytate and CAP complexes to effectively inhibit the demineralization of the enamel slices. This was seen especially at higher pH levels as occurred with glucose at 5.6 mM and with slices exposed to CAP complexes with intermediate arginine and calcium levels.

TABLE 7

Calcium released from tooth enamel slices incubated in 1M acetic acid buffer 5.0 in the presence of arginine phytate and the various CAP salts.

| Compound tested | Calcium ($\mu$g/ml) Mean ± SEM | % inhibition |
|---|---|---|
| $CAP_0$ | 232.0 ± 3.8 | 61.9 |
| $CAP_1$ | 313.3 ± 14.2 | 48.6 |
| $CAP_2$ | 250.6 ± 13.8 | 58.9 |
| $CAP_3$ | 235.2 ± 2.8 | 61.4 |
| $CAP_4$ | 170.1 ± 23.7 | 72.1 |
| $CAP_5$ | 115.9 ± 15.5 | 81.0 |
| Phytate | 318.9 ± 30.3 | 47.7 |
| Control | 609.3 ± 49.5 | 0.0 |

TABLE 8

Phosphorus released from tooth enamel slices incubated in 1M acetic acid buffer pH 5.0 in the presence of arginine phytate and the various CAP salts.

| Compound tested | Phosphorus ($\mu$g/ml) Mean ± SEM | % inhibition |
|---|---|---|
| $CAP_0$ | 70.0 ± 17.4 | 60.8 |
| $CAP_1$ | 89.3 ± 21.7 | 50.0 |
| $CAP_2$ | 69.7 ± 14.6 | 60.9 |
| $CAP_3$ | 77.9 ± 14.5 | 56.4 |
| $CAP_4$ | 55.2 ± 9.9 | 69.1 |
| $CAP_5$ | 44.5 ± 2.5 | 75.1 |
| Phytate | 109.1 ± 35.9 | 43.9 |
| Control | 178.6 ± 57.6 | 0.0 |

TABLE 9

Scoring of enamel demineralization after 8 h incubation in 1M acetic acid buffer pH 4.0, 5.0 and 6.0 in the presence of arginine phytate and the various CAP salts.

| Compound | Score Acetic acid pH 4.0 | Acetic acid pH 5.0 | Acetic acid pH 6.0 | Overall mean score | Percent inhibition |
|---|---|---|---|---|---|
| $CAP_0$ | 2.0 | 1.0 | 0.0 | 1.0 | 62.5% |
| $CAP_1$ | 2.0 | 0.0 | 1.0 | 1.0 | 62.5% |
| $CAP_2$ | 2.0 | 0.0 | 0.0 | 0.67 | 75.0% |
| $CAP_3$ | 2.0 | 1.0 | 0.0 | 1.0 | 62.5% |
| $CAP_4$ | 1.0 | 0.0 | 0.0 | 0.33 | 89.5% |
| $CAP_5$ | 1.0 | 1.0 | 0.0 | 0.67 | 75.0% |
| Phytate | 2.0 | 1.0 | 1.0 | 1.33 | 50.0% |
| Control | 3.0 | 3.0 | 2.0 | 2.67 | 0% |

EXAMPLE IV

This example demonstrates the ability of an oral composition containing calcium, arginine and bicarbonate/carbonate (CABC) to retard the demineralization of enamel in vitro. Specifically, this example shows the ability of calcium, arginine and bicarbonate/carbonate composition to raise the pH of a severely acidic condition (which is produced in vivo as a result of their catabolism of fermentable sugars present at high concentration and for prolonged periods of time) to a pH where base formation from arginine can optimally occur. It also demonstrates retardation of the demineralization of powdered enamel and dentine incubated with the oral bacteria and sugar source. The salivary sediment model system used in Example III was used in these experiments except that the demineralization assay used powdered enamel from the crowns of human teeth rather than tooth slices.

The powdered enamel was prepared according to the flotation method of Manly and Hodge (1939) *J. dent. Res.* 18, 133–141 which is incorporated herein by reference. Initially, permanent teeth were carefully cleaned and then pulverized to a fine powder in a ball-mill and sifted through 60 mesh to remove the larger particles. The sifted tooth powder was then separated by density fractionation using a bromoform/acetone mixture of ratio 91% bromoform and 9% acetone (v/v) which gave a density of 2.70. The enamel fractions (density 2.9–3.0) were heavier. The enamel fraction were removed after centrifugation, washed with the bromoform/acetone mixture and dried by evaporation.

Five incubation mixtures containing salivary sediment at 16.7% (v/v) and glucose at 11.2 mM each, with a total volume of 2.4 ml were prepared. Each mixture was incubated for three hours at 37° C. and the pH was measured at 0, 0.5, 1, 2 and 3 hours. At the end of the three hours, each incubation mixture was equally divided into four incubation mixtures (600 $\mu$l each). To each one of the mixtures in one set of four, 1 mg arginine bicarbonate and 1 mg calcium carbonate were similarly added as a mixed powder. To the second set, 0.5 mg of arginine bicarbonate and 0.5 mg of calcium carbonate were similarly added to each mixture. In the third set, 1 mg of arginine bicarbonate was added; in the fourth set, 1 mg of calcium carbonate was added. No addition was made to the fifth set. All of the mixtures were prepared in an ice bath and then transferred immediately to a water bath at 37° C. where they were incubated for 0, 0.5, 1.5 and 3 hours with occasional shaking.

The pH was recorded in one tube taken at each time interval from each set, which was then divided into two. One half was retained and stored at 4° C. for subsequent analysis of calcium and phosphate. Duplicate samples (60 $\mu$l) were removed for this purpose. The other half was added to 1 mg of tooth powder and incubated for 2 hours at 37° C. to assess the solubilization ability. Undissolved tooth powder after 2 hours was separated from the aqueous phase as a pellet by centrifugation in a micro-centrifuge (152 Microfuge, Beckman) at 7700 g for 3 minutes. The supernatant of each sample was carefully removed by suction and stored at 4° C. for subsequent analysis for calcium and for phosphate as described above. The tooth powder pellet was dissolved in hydrochloric acid and duplicate samples (60 $\mu$l) were withdrawn for similar calcium and phosphate analyses.

Figure 3:
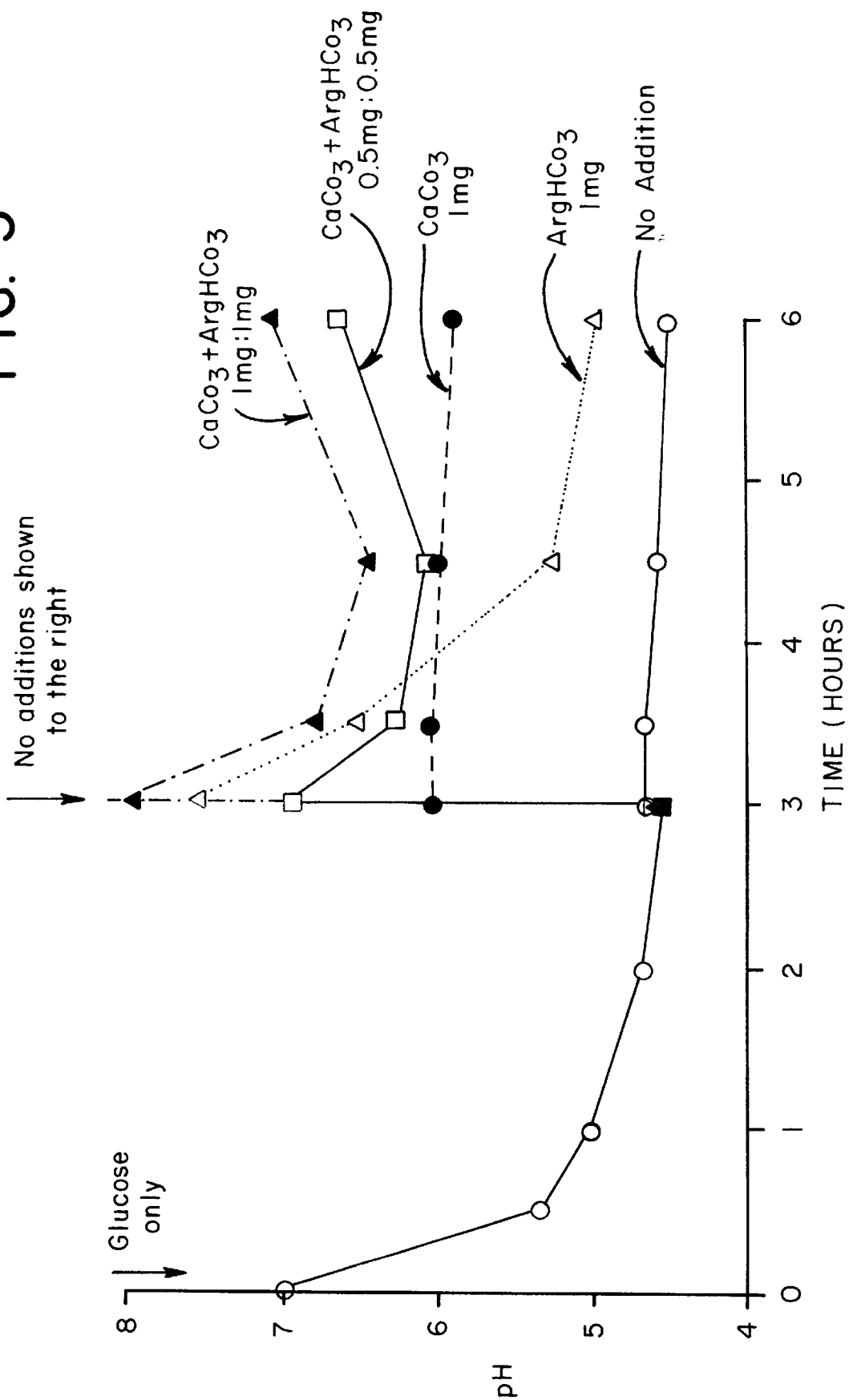
FIG. 3 shows the pH response of salivary sediment incubated with 11.2 mM glucose three hours before and three hours after calcium, arginine and cariostatic anion were added to the incubation mixture. The cariostatic anion added was carbonate/bicarbonate. Controls included calcium carbonate, arginine bicarbonate and neither.

The pH changes for the full six hours of incubation are shown in FIG. 3. During the first three hours, the pH rapidly fell and reached a minimum of 4.65. During the second three hours, the pH fell further to 4.51 in the no addition control. Upon addition of the arginine bicarbonate and/or the calcium carbonate, the pH immediately rose. The most significant rise in pH occurred in mixtures containing both arginine bicarbonate and calcium carbonate (CABC). Arginine bicarbonate also gave an initial rapid rise in the pH but could not maintain a rise in pH sufficient to overcome the severe and prolonged acidity present, which is characteristic of highly caries prone dentition sites. Calcium carbonate also raised the pH rapidly but did so to a lesser extent than the other compositions and showed no subsequent rise.

Analysis of the tooth powders showed 20% solubilization during the first three hour period of incubation when the pH fell from 7.0 to 4.65 and further 12% solubilization during the second three hour period of incubation where the pH fell further to 4.51 (total of 32% solubilization). With the calcium carbonate addition, only 9% further solubilization occurred during the second period. With arginine bicarbonate, the further solubilization was 16%. By contrast, the calcium bicarbonate/arginine bicarbonate (1:1) combination not only showed no further solubilization but showed instead regain of the 20% loss observed during the first three hour period of incubation (total of 0% solubilization). The other calcium carbonate/arginine bicarbonate (0.5:0.5) combination showed less of an effect. It showed 2% of further solubilization during the second period.

The pH results demonstrated the ability of the CABC composition to counter the reduction in the pH in the oral cavity produced during the catabolism of glucose and its ability to raise the pH sufficiently to enable the arginine in the CABC composition to produce base and continue raising the pH. This example further demonstrates the ability of the compositions described by the present invention to provide a means to retard or prevent tooth solubilization and reduce or prevent dental caries.

We claim:

1. An oral composition comprising calcium, arginine, and bicarbonate distributed in an oral vehicle in an amount sufficient to reduce dental caries.

2. The oral composition according to claim 1 wherein said composition contains arginine in an amount ranging from 5 $\mu$g/mg to 700 $\mu$g/mg.

3. The oral composition according to claim 1 wherein said oral composition contains calcium in an amount ranging from 5 $\mu$g/mg to 200 $\mu$g/mg.

4. The oral composition according to claim 1 wherein said oral composition contains bicarbonate in an amount ranging from 5 $\mu$g/mg to 200 $\mu$g/mg.

5. The oral composition according to claim 1 wherein the calcium is provided as a salt selected from the group consisting of calcium carbonate, calcium bicarbonate, and calcium organic phosphate.

6. The oral composition according to claim 1 wherein the arginine is provided as a salt selected from the group consisting of arginine bicarbonate, arginine carbonate, and arginine organic phosphate.

7. A method for preparing the oral composition of claim 1 comprising the sequential steps of:
   (a) titrating a bicarbonate solution with arginine hydroxide in an amount and under conditions sufficient to form an arginine bicarbonate complex; and
   (b) titrating said arginine bicarbonate complex with calcium carbonate in an amount sufficient to form a calcium arginine bicarbonate complex.

8. A method for preparing the oral composition of claim 1 comprising the sequential steps of:
   (a) titrating a bicarbonate solution with arginine hydroxide in an amount and under conditions sufficient to form an arginine bicarbonate complex; and
   (b) titrating said arginine bicarbonate complex with saturated calcium hydroxide to form a calcium arginine bicarbonate complex.

9. A method for retarding dental caries comprising delivering a therapeutically effective amount of the oral composition of claim 1 into the oral cavity.

10. The oral composition according to claim 1 wherein the pH is between 5 and 9.

11. An oral composition comprising calcium, arginine, and carbonate distributed in an oral vehicle in an amount sufficient to reduce dental caries.

12. The oral composition according to claim 11 wherein said composition contains arginine in an amount ranging from 5 $\mu$g/mg to 700 $\mu$g/mg.

13. The oral composition according to claim 11 wherein said oral composition contains calcium in an amount ranging from 5 $\mu$g/mg to 200 $\mu$g/mg.

14. The oral composition according to claim 11 wherein said oral composition contains carbonate in an amount ranging from 5 $\mu$g/mg to 200 $\mu$g/mg.

15. The oral composition according to claim 11 wherein the calcium is provided as a salt selected from the group consisting of calcium carbonate, calcium bicarbonate, and calcium organic phosphate.

16. The oral composition according to claim 11 wherein the arginine is provided as a salt selected from the group consisting of arginine bicarbonate, arginine carbonate, and arginine organic phosphate.

17. A method for preparing the oral composition of claim 11 comprising the sequential steps of:
   (a) titrating a carbonate solution with arginine hydroxide in an amount and under conditions sufficient to form an arginine carbonate complex; and
   (b) titrating said arginine carbonate complex with calcium carbonate in an amount sufficient to form a calcium arginine carbonate complex.

18. A method for preparing the oral composition of claim 11 comprising the sequential steps of:
   (a) titrating a carbonate solution with arginine hydroxide in an amount and under conditions sufficient to form an arginine carbonate complex; and
   (b) titrating said arginine carbonate complex with saturated calcium hydroxide to form a calcium arginine carbonate complex.

19. A method for retarding dental caries comprising delivering a therapeutically effective amount of the oral composition of claim 11 into the oral cavity.

20. The oral composition according to claim 11 wherein the pH is between 5 and 9.

21. An oral composition comprising calcium, arginine, and a cariostatic anion distributed in an oral vehicle in an amount sufficient to reduce dental caries.

22. The oral composition according to claim 21 wherein said oral composition further comprises a therapeutically effective amount of fluoride.

23. The oral composition according to claim 21 wherein said composition contains arginine in an amount ranging from 5 $\mu$g/mg to 700 $\mu$g/mg.

24. The oral composition according to claim 21 wherein said oral composition contains calcium in an amount ranging from 5 $\mu$g/mg to 200 $\mu$g/mg.

25. The oral composition according to claim 21 wherein said oral composition contains one or more cariostatic anions in an amount ranging from 5 $\mu$g/mg to 200 $\mu$g/mg.

26. The oral composition according to claim 21 wherein said oral composition is a dental care product.

27. An oral composition according to claim 21 wherein said oral composition is a food product.

28. The oral composition according to claim 21 wherein said oral composition is chewing gum.

29. An oral composition comprising an oral vehicle and active ingredients, wherein said active ingredients consist essentially of calcium, arginine, and a cariostatic anion, said active ingredients being present in said oral composition in an amount sufficient to reduce dental caries.

30. An oral composition comprising an oral vehicle and active ingredients, wherein said active ingredients consist essentially of calcium, arginine, bicarbonate, and fluoride, said active ingredients being present in said oral composition in an amount sufficient to reduce dental caries.

* * * * *